United States Patent [19]

Bunnell et al.

[11] Patent Number: 5,703,232
[45] Date of Patent: Dec. 30, 1997

[54] PROCESS AND SOLVATE OF 2-METHYL-THIENO-BENZODIAZEPINE

[75] Inventors: Charles A. Bunnell, Lafayette, Ind.; Terrence Michael Hotten, Farnborough, England; Samuel D. Larsen, West Lafayette, Ind.; David Edward Tupper, Reading, England

[73] Assignee: Eli Lilly and Company, Indianapolis, Ind.

[21] Appl. No.: 586,431

[22] Filed: Jan. 16, 1996

Related U.S. Application Data

[62] Division of Ser. No. 410,474, Mar. 24, 1995, Pat. No. 5,631,250.

[51] Int. Cl.[6] ............... C07D 243/10; C07D 495/04
[52] U.S. Cl. ............................................. 540/557
[58] Field of Search ........................ 514/220; 540/557

[56] References Cited

U.S. PATENT DOCUMENTS

| | | | |
|---|---|---|---|
| 4,115,568 | 9/1978 | Chakrabarti et al. | 424/250 |
| 4,115,574 | 9/1978 | Chakrabarti et al. | 424/250 |
| 4,237,279 | 12/1980 | Fisher | 544/16 |
| 5,229,382 | 7/1993 | Chakrabarti et al. | 514/220 |
| 5,439,888 | 8/1995 | Shuman et al. | 514/18 |

OTHER PUBLICATIONS

J. K. Chakrabarti et al., *J. Med. Chem.*, 23, (1980), 878–884.

*Primary Examiner*—Mukund J. Shah
*Assistant Examiner*—Brenda Coleman
*Attorney, Agent, or Firm*—MaCharri Vorndran-Jones; David E. Boone

[57] ABSTRACT

The invention provides lower alcohol solvates of 2-methyl-4-(4-methyl-1-piperazinyl)-10H-thieno[2,3-b][1,5]benzodiazepine (olanzapine) and a process for making such lower alcohol solvates of olanzapine. The invention provides a method for using such solvates of olanzapine to prepare substantially pure anhydrous Form I 2-methyl-thieno-benzodiazepine.

8 Claims, No Drawings

PROCESS AND SOLVATE OF 2-METHYL-THIENO-BENZODIAZEPINE

This application is a division of application Ser. No. 08/410,474 filed Mar. 24, 1995 now U.S. Pat. No. 5,631,250.

FIELD OF THE INVENTION

This invention relates to lower alcohol solvates of 2-methyl-4-(4-methyl-1-piperazinyl)-10H-thieno[2,3-b][1,5]benzodiazepine (olanzapine) and a process for using such lower alcohol solvates of olanzapine to prepare olanzapine which is useful for making desired Form I 2-methyl-4-(4-methyl-1-piperazinyl)-10H-thieno[2,3-b][1,5]benzodiazepine

BACKGROUND OF THE INVENTION

Anhydrous Form I 2-methyl-4-(4-methyl-1-piperazinyl)-10H-thieno[2,3-b][1,5]benzodiazepine compound has useful central nervous system activity.

Applicants have discovered that 2-methyl-4-(4-methyl-1-piperazinyl)-10H-thieno[2,3-b][1,5]benzodiazepine (olanzapine) exists in two anhydrous forms which are clearly distinguishable by X-ray powder diffractometry. Unfortunately, anhydrous Form II olanzapine is metastable and is therefore not well suited for commercial use in pharmaceutical formulations. However, surprisingly and in accordance with the invention, it has now been discovered that the second polymorph of 2-methyl-4-(4-methyl-1-piperazinyl)-10H-thieno[2,3-b][1,5]benzodiazepine, designated as anhydrous Form I olanzapine, is stable and is therefore well adapted for commercial use in pharmaceutical formulations.

It is desirable to prepare the substantially pure anhydrous Form I crystalline 2-methyl-4-(4-methyl-1-piperazinyl)-10H-thieno[2,3-b][1,5]benzodiazepine to assure uniformity of product. Anhydrous Form I 2-methyl-4-(4-methyl-1-piperazinyl)-10H-thieno[2,3-b][1,5]benzodiazepine can be prepared via a convenient, efficient, and ecologically acceptable process which utilizes the lower alcohol solvates of olanzapine claimed herein.

The crystalline anhydrous Form I 2-methyl-4-(4-methyl-1-piperazinyl)-10H-thieno[2,3-b][1,5]benzodiazepine (Form I) and process for preparing Form I are particularly important for the commercial development of the pharmaceutically active anhydrous Form I 2-methyl-4-(4-methyl-1-piperazinyl)-10H-thieno[2,3-b][1,5]benzodiazepine.

The present invention provides the desired lower alcohol solvates of olanzapine which are particularly useful for preparing the desired anhydrous Form I olanzapine.

SUMMARY OF THE INVENTION

The present invention provides a compound selected from the group consisting of a methanol, ethanol, and 1-propanol crystalline solvates of 2-methyl-4-(4-methyl-1-piperazinyl)-10H-thieno[2,3-b][1,5]benzodiazepine (olanzapine).

The present invention provides a process for preparing anhydrous Form I comprising contacting a lower alcohol solvate with a solvent selected from the group consisting of ethyl acetate, acetone, 2-propanol, t-butanol, tetrahydrofuran, and toluene.

The present invention provides a new method for preparing a lower alcohol solvate of olanzapine. The process provides greater yields of the desired product, eleminates tedious separation steps, and provides a product that is easy to handle for production purposes.

DETAILED DESCRIPTION OF THE INVENTION

Applicants have discovered that 2-methyl-4-(4-methyl-1-piperazinyl)-10H-thieno[2,3-b][1,5]benzodiazepine, which is a compound of Formula(I):

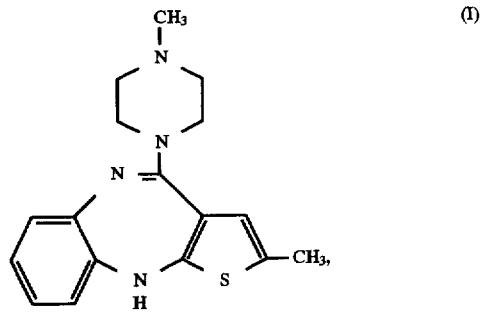

exists as two different anhydrous forms which are distinguishable by x-ray powder diffractometry. As discussed supra., the two forms have been designated Form I and Form II. For stable commercial pharmaceutical preparations, purified anhydrous Form I 2-methyl-4-(4-methyl-1-piperazinyl)-10H-thieno[2,3-b][1,5]benzodiazepine (Form I) must be substantially free from undesired polymorphs.

As used herein "substantially pure" shall refer to the desired polymorph associated with <5% about undesired polymorph; and most preferably it shall refer to <2% about undesired polymorph. It is further preferred that "substantially pure" shall refer to < about 0.5% related substances. The term "desired" shall refer to the polymorph claimed as "substantially pure". For example "substantially pure Form I" shall mean < about 5% non-Form I polymorph and >95% Form I. When the polymorph is formulated in a pharmaceutical formulation, then the term "substantially pure" shall refer to about <10% undesired polymorph. More preferably, when the polymorph is formulated, the term "substantially pure" shall refer to < about 5% undesired polymorph.

As used herein, the term "mixing" refers to contacting the components to be mixed wherein such action provides particle size reduction. It may be prefered that the term "mixing" shall refer to; however, is not limited to grinding, pulverizing, contacting with aggitation, or an action providing a formation of powdered particles.

As used herein, the term "crystallization solvent" shall refer to one or more selected from the group consisting of aromatic hydrocarbons, $C_3$–$C_9$ ketones, $C_3$–$C_9$ branched alcohols, $C_3$–$C_9$ esters, $C_5$–$C_9$ hydrocarbons, $C_3$–$C_9$ ethers, and cyclic ethers. The term "aromatic hydrocarbon" refers to a $C_4$–$C_6$ alkyl aromatic solvent which may include substituted aromatics. Examples of aromatic hydrocarbons include, but are not limited to toluene, benzene, and the like. The term "$C_5$–$C_9$ hydrocarbons" refer to $C_5$–$C_9$ alkyl solvents which may be substituted, branched or unbranched alkyl. Such hydrocarbon solvents include, but are not limited to straight or branched heptane, octane, pentane, and the like.

The term "$C_3$–$C_9$ ketones" refers to straight or branched ketones which may optionally be substituted. The term "$C_3$–$C_9$ esters" refers to straight or branched esters which may optionally be substituted. The term "ethers" refer to lower alkyl ($C_2$–$C_8$) alkyl ethers which may be straight, branched or substituted. The term ether shall include but is not limited to, for example, t-butyl methylether, and the like.

The term "cyclic ether" shall refer to a $C_5$–$C_7$ cyclic ether which may be optionally substituted. It is especially preferred that the ether solvent is dry. It is particularly preferred that such dry solvent shall contain less than about 1% water.

As used herein, the term "substituted" shall refer to from about one to about three non-hydrocarbon substituents which may be selected from the group consisting, for example, of $CF_3$, Cl, Br, F, I, and the like. When the solvent includes a Cl substituent, then the solvent molecule shall additionally include at least two carbon atoms. The suggested substituents are in no way exhaustive. Applicants envision that other non-hydrocarbon substituents will provide crystallization solvents having the desired characteristics set forth below.

The crystallization solvents are selected with the requirements that 1) 2-methyl-4-(4-methyl-1-piperazinyl)-10H-thieno[2,3-b][1,5]benzodiazepine must be at least partially soluble in the solvent selected; and 2) the solvent selected must not form a solvate with 2-methyl-4-(4-methyl-1-piperazinyl)-10H-thieno[2,3-b][1,5]benzodiazepine. Most preferably, the solvate shall dissolve in the solvent before the crystallization process is begun.

Especially preferred solvents for the crystallization process are one or more selected from the group consisting of ethyl acetate, acetone, 2-propanol, tetrahydrofuran, and toluene.

As used herein, the term "lower alcohol" shall refer to $C_1$–$C_3$ alcohol. Therefore, the term includes methanolate, ethanolate and 1-propanolate.

As used herein, the term "2-methyl-4-(4-methyl-1-piperazinyl)-10H-thieno[2,3-b][1,5]benzodiazepine" refers to a technical grade of 2-methyl-4-(4-methyl-1-piperazinyl)-10H-thieno[2,3-b][1,5]benzodiazepine when no specific solvate or polymorph is named. Typically, the technical grade olanzapine contains at least about 2% undesired polymorph.

The term "technical grade" refers to a grade of olanzapine which has not been through the final purification and may contain undesired polymorphs and/or impurity levels.

Anhydrous Form I olanzapine has a typical X-ray powder diffraction pattern substantially as follows, using a Siemen's D5000 diffractometer which is equipped with a copper radiation source, wherein d represents the interplaner spacing:

| d | $I/I_1$ |
|---|---|
| 10.2689 | 100.00 |
| 8.577 | 7.96 |
| 7.4721 | 1.41 |
| 7.125 | 6.50 |
| 6.1459 | 3.12 |
| 6.071 | 5.12 |
| 5.4849 | 0.52 |
| 5.2181 | 6.86 |
| 5.1251 | 2.47 |
| 4.9874 | 7.41 |
| 4.7665 | 4.03 |
| 4.7158 | 6.80 |
| 4.4787 | 14.72 |
| 4.3307 | 1.48 |
| 4.2294 | 23.19 |
| 4.141 | 11.28 |
| 3.9873 | 9.01 |
| 3.7206 | 14.04 |
| 3.5645 | 2.27 |
| 3.5366 | 4.85 |
| 3.3828 | 3.47 |
| 3.2516 | 1.25 |
| 3.134 | 0.81 |
| 3.0848 | 0.45 |
| 3.0638 | 1.34 |
| 3.0111 | 3.51 |
| 2.8739 | 0.79 |
| 2.8102 | 1.47 |

-continued

| d | $I/I_1$ |
|---|---|
| 2.7217 | 0.20 |
| 2.6432 | 1.26 |
| 2.6007 | 0.77 |

Anhydrous Form II olanzapine (Form II) has a typical X-ray powder diffraction pattern substantially as follows, using a Siemen's D5000 diffractometer having a copper radiation source, wherein d represents the interplaner spacing:

| d | $I/I_1$ |
|---|---|
| 9.9463 | 100.00 |
| 8.5579 | 15.18 |
| 8.2445 | 1.96 |
| 6.8862 | 14.73 |
| 6.3787 | 4.25 |
| 6.2439 | 5.21 |
| 5.5895 | 1.10 |
| 5.3055 | 0.95 |
| 4.9815 | 6.14 |
| 4.8333 | 68.37 |
| 4.7255 | 21.88 |
| 4.6286 | 3.82 |
| 4.533 | 17.83 |
| 4.4624 | 5.02 |
| 4.2915 | 9.19 |
| 4.2346 | 18.88 |
| 4.0855 | 17.29 |
| 3.8254 | 6.49 |
| 3.7489 | 10.64 |
| 3.6983 | 14.65 |
| 3.5817 | 3.04 |
| 3.5064 | 9.23 |
| 3.3392 | 4.67 |
| 3.2806 | 1.96 |
| 3.2138 | 2.52 |
| 3.1118 | 4.81 |
| 3.0507 | 1.96 |
| 2.948 | 2.40 |
| 2.8172 | 2.89 |
| 2.7589 | 2.27 |
| 2.6597 | 1.86 |
| 2.6336 | 1.10 |
| 2.5956 | 1.73 |

The x-ray powder diffraction patterns set forth herein were obtained with a copper k of wavelength=1.541 Å. The interplanar spacings in the column marked "d" are in Angstroms. The typical relative intensities are in the column marked "$I/I_1$". The diffractometer was equipped with Kevex silicon lithium solid state detector.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

As used herein, the term "solvate" shall refer to a true solvate of olanzapine, wherein the solvent molecule is held within the crystalline latice.

A preferred embodiment of the invention is the crystalline mono(methanol) solvate of 2-methyl-4-(4-methyl-1-piperazinyl)-10H-thieno[2,3-b][1,5]benzodiazepine exhibiting substantially the x-ray powder diffraction pattern of Table 1:

TABLE 1

Mono (methanol) Solvate

| d | I/I₁ |
|---|---|
| 10.2932 | 100.00 |
| 9.4747 | 3.09 |
| 7.1794 | 0.97 |
| 7.0601 | 2.31 |
| 6.2612 | 1.89 |
| 5.7558 | 1.27 |
| 5.4197 | 5.36 |
| 5.2317 | 1.32 |
| 5.1348 | 0.46 |
| 5.1285 | 1.04 |
| 5.0506 | 1.57 |
| 5.0331 | 1.43 |
| 4.7672 | 2.22 |
| 4.7137 | 7.46 |
| 4.4533 | 6.03 |
| 4.3315 | 3.28 |
| 4.2656 | 2.66 |
| 4.044 | 3.37 |
| 3.9821 | 0.95 |
| 3.9696 | 1.20 |
| 3.9532 | 0.88 |
| 3.9125 | 1.09 |
| 3.8562 | 7.85 |
| 3.7983 | 4.23 |
| 3.7378 | 1.34 |
| 3.7059 | 3.03 |
| 3.6384 | 1.06 |
| 3.6028 | 5.36 |
| 3.5216 | 2.75 |
| 3.4454 | 0.62 |
| 3.4321 | 0.53 |
| 3.4193 | 0.60 |
| 3.248 | 0.90 |
| 3.2416 | 1.18 |
| 3.1347 | 0.88 |
| 3.127 | 0.74 |
| 3.0121 | 0.65 |
| 2.9979 | 0.83 |
| 2.9767 | 0.92 |
| 2.9303 | 0.53 |
| 2.9172 | 0.58 |
| 2.8048 | 0.55 |
| 2.7483 | 0.79 |
| 2.7412 | 0.83 |

The x-ray powder diffraction pattern in Table I was obtained with a copper $K_\alpha$ of wavelength $\lambda=1.54184$ Å. The interplanar spacings are in the column marked "d" are in Angstroms. The typical relative intensities are in the column marked "$I/I_1$".

Another preferred embodiment of the present invention is the crystalline mono(ethanol)solvate of 2-methyl-4-(4-methyl-1-piperazinyl)-10H-thieno[2,3-b][1,5] benzodiazepine exhibiting substantially the x-ray powder diffraction pattern of Table 2:

TABLE 2

Mono (ethanol) solvate

| d | I/I₁ |
|---|---|
| 10.2672 | 100.00 |
| 9.6467 | 1.48 |
| 7.2319 | 2.92 |
| 6.5065 | 1.61 |
| 5.9172 | 0.69 |
| 5.6475 | 1.02 |
| 5.5197 | 2.48 |
| 5.1492 | 4.20 |
| 4.7926 | 2.82 |
| 4.6477 | 0.54 |
| 4.4450 | 4.95 |
| 4.3473 | 2.04 |
| 4.2726 | 0.55 |
| 4.1290 | 2.84 |
| 3.9908 | 2.90 |
| 3.8338 | 1.83 |
| 3.6932 | 1.61 |
| 3.6189 | 1.52 |
| 3.5070 | 0.63 |
| 3.4389 | 8.58 |
| 3.3083 | 0.80 |
| 3.2618 | 0.55 |
| 3.1950 | 0.91 |
| 3.1050 | 0.65 |
| 3.0761 | 0.54 |
| 3.0477 | 0.47 |
| 2.9835 | 0.60 |
| 2.9292 | 0.54 |
| 2.8703 | 0.58 |
| 2.8215 | 0.59 |
| 2.7852 | 2.59 |
| 2.6908 | 0.57 |
| 2.6287 | 0.75 |
| 2.5791 | 5.54 |

Another preferred embodiment of the invention is the crystalline mono(1-propanol)solvate of 2-methyl-4-(4-methyl-1-piperazinyl)-10H-thieno[2,3-b][1,5] benzodiazepine exhibiting substantially the x-ray diffraction patterns of Table 3:

TABLE 3

Mono (1-propanol) solvate

| d | I/I₁ |
|---|---|
| 10.2736 | 100.00 |
| 9.6086 | 1.13 |
| 7.9084 | 0.72 |
| 7.3331 | 2.41 |
| 6.6530 | 5.33 |
| 6.1030 | 0.79 |
| 5.6758 | 6.47 |
| 5.2990 | 1.70 |
| 5.1333 | 1.98 |
| 4.9632 | 14.61 |
| 4.8014 | 3.14 |
| 4.6691 | 2.22 |
| 4.5756 | 1.62 |
| 4.4451 | 9.51 |
| 4.1821 | 1.03 |
| 4.0883 | 3.58 |
| 3.9890 | 1.26 |
| 3.9021 | 1.80 |
| 3.8234 | 3.38 |
| 3.7258 | 1.22 |
| 3.6785 | 1.27 |
| 3.6033 | 1.22 |
| 3.5265 | 0.94 |
| 3.4234 | 1.85 |
| 3.3653 | 0.48 |
| 3.3121 | 1.38 |
| 3.2125 | 0.67 |
| 3.1795 | 0.61 |
| 3.1230 | 0.47 |
| 3.0435 | 1.06 |
| 2.9461 | 1.74 |
| 2.8951 | 0.81 |
| 2.8495 | 1.68 |
| 2.7744 | 0.66 |

TABLE 3-continued

| Mono (1-propanol) solvate | |
|---|---|
| d | I/I$_1$ |
| 2.7445 | 0.62 |
| 2.7140 | 0.47 |
| 2.6609 | 0.48 |
| 2.6110 | 0.68 |
| 2.5683 | 2.36 |

The x-ray powder diffraction data in Tables 2 and 3 was collected employing an Enraf-Nonius CAD4 kappa axis diffractometer. The diffraction pattern was obtained with a copper k of wavelength=1.542Å. The interplanar spacings in the column marked "d" are expressed in Angstroms. The typical relative intensities are in the column marked "I/I$_1$".

The compounds and processes of the present invention are useful for preparing compounds having beneficial central nervous system activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of this invention include the following:

A) A mono (ethanol) solvate of 2-methyl-4-(4-methyl-1-piperazinyl)-10H-thieno[2,3-b][1,5]benzodiazepine
B) Substantially pure refers to ≦5% undesired polymorph;
C) Substantially pure refers to ≦2% undesired polymorph;
D) A mono (methanol) solvate of olanzapine;
E) A mono (1-propanol) solvate of olanzapine;
F) A substantially pure solvate of olanzapine selected from the group consisting of mono (methanol), mono (ethanol), and mono (1-propanol).

The Form I olanzapine prepared by the process of this invention has useful central nervous system activity. This activity has been demonstrated using well-established procedures. For example, the anhydrous Form I compound has been assessed in a number of standard behavior tests predictive of antipsychotic activity. The claimed compound antagonised apomorphine-induced climbing behavior and hypothermia in mice. See Moore, N. A. et al *Psychopharmacology* 94 (2), 263-266 (1988). The compound also inhibits conditioned avoidance response in rats, but unlike standard antipsychotic compounds, the compound of this invention induces cataleptsy only at higher doses. This separation between the doses required to block conditioned avoidance response and to induce catalepsy indicates that the compound is less likely to induce extrapyramidal side effects in the clinic.

In addition, anhyrous Form I olanzapine has been found to have a favorable profile of activity in a number of in vitro binding assays, designed to measure the degree of binding to neural receptors. For example, the compound is active at the dopamine D-1 and D-2 receptors as indicated by an IC50 of less than 1 μM in the 3H-SCH233390 (Billard, et al. Life Sciences 35:1885 (1984)) and the 3H spiperone (Seeman et al Nature 216:717 (1976)) binding assays respectively.

Further, the compound is active at the 5-HT-2 receptor and 5-HT1C receptor. The in vitro results would indicate that the compound is effective in the treatment of psychotic conditions but less likely to induce extra pyramidal side-effects.

As used herein the term "psychosis" shall mean pathologic psychological conditions which are psychoses or may be associated with psychotic features including, but not limited to the following disorders which have been characterized in the DSM-III-R. *Diagnostic and Statistical Manual of Mental Disorders, Revised,* 3rd Ed. (1980). The DSM-III-R was prepared by the Task Force on Nomenclature and Statistics of the American Psychiatric Association, and provides clear descriptions of diagnostic catagories. The numbers in parenthesis refer to the DSM-III-R categories. The skilled artisan will recognize that there are alternative nomenclatures, nosologies, and classification systems for pathologic psychological conditions and that these systems evolve with medical scientific progress.

Examples of pathologic psychologic conditions which may be treated using anhydrous Form I 2-methyl-4-(4-methyl-1-piperazinyl)-10H-thieno[2,3-b][1,5]benzodiazepine include, but are not limited to, Conduct Disorder, Group Type (312.20), Conduct Disorder, Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Multi-infarct dementia, with Delirium (290.41), Multi-infarct dementia, with Delusions (290.42), Multi-infarct dementia, with Depression (290.43), Multi-infarct dementia, Uncomplicated (290.40), Senile Dementia NOS (290.00), Presenile Dementia NOS (290.10), Alcohol Withdrawal Delirium (291.00), Alcohol Hallucinosis (291.30), Alcohol Dementia Associated with Alcoholism (291.20), Amphetamine or Similarly Acting Sympathomimetic Intoxication (305.70), Amphetamine or Similarly Acting Sympathomimetic Delirium (292.81), Amphetamine or Similarly Acting Sympathomimetic Delusional Disorder (292.11), Cannabis Delusional Disorder (292.11), Cocaine Intoxication (305.60), Cocaine Delirium (292.81), Cocaine Delusional Disorder (292.11), Hallucinogen Hallucinosis (305.30), Hallucinogen Delusional Disorder (292.11), Hallucinogen Mood Disorder (292.84), Hallucinogen Posthallucinogen Perception Disorder (292.89), Phencyclidine (PCP) or Similarly Acting Arylcyclohexylamine Intoxication (305.90), Phencyclidine (PCP) or Similarly Acting Arylcyclohexylamine Delirium (292.81), Phencyclidine (PCP) or Similarly Acting Arylcyclohexylamine Delusional Disorder (292.11), Phencyclidine (PCP) or Similarly Acting Arylcyclohexylamine Mood Disorder (292.84), Phencyclidine (PCP) or Similarly Acting Arylcyclohexylamine Organic Mental Disorder NOS (292.90), Other or Unspecified Psychoactive Substance Intoxication (305.90), Other or Unspecified Psychoactive Substance Delirium (292.81), Other or Unspecified Psychoactive Substance Dementia (292.82), Other or Unspecified Psychoactive Substance Delusional Disorder (292.11), Other or Unspecified Psychoactive Substance Hallucinosis (292.12), Other or Unspecified Psychoactive Substance Mood Disorder (292.84), Other or Unspecified Psychoactive Substance Anxiety Disorder (292.89), Other or Unspecified Psychoactive Substance Personality Disorder (292.89), Other or Unspecified Psychoactive Substance Organic Mental Disorder NOS (292.90), Delirium (293.00), Dementia (294.10), Organic Delusional Disorder (293.81), Organic Hallucinosis (293.82), Organic Mood Disorder (293.83), Organic Anxiety Disorder (294.80), Organic Mental Disorder (294.80), Obsessive Compulsive Disorder (300.30), Post-traumatic Stress Disorder (309.89), Generalized Anxiety Disorder (300.02), Anxiety Disorder NOS (300.00), Body Dysmorphic Disorder (300.70), Hypochondriasis (or Hypochondriacal Neurosis) (300.70), Somatization Disorder (300.81), Undifferentiated Somatoform Disorder (300.70), Somatoform Disorder NOS (300.70), Intermittent Explosive Disorder (312.34), Kleptomania (312.32), Pathological Gambling (312.31), Pyromania (312.33), Trichotillomania (312.39), and Impulse Control Disorder NOS (312.39).

Schizophrenia, Catatonic, Subchronic, (295.21), Schizophrenia, Catatonic, Chronic (295.22), Schizophrenia, Catatonic, Subchronic with Acute Exacerbation (295.23), Schizophrenia, Catatonic, Chronic with Acute Exacerbation (295.24), Schizophrenia, Catatonic, in Remission (295.55), Schizophrenia, Catatonic, Unspecified (295.20), Schizophrenia, Disorganized, Subchronic (295.11), Schizophrenia, Disorganized, Chronic (295.12), Schizophrenia, Disorganized, Subchronic with Acute Exacerbation (295.13), Schizophrenia, Disorganized, Chronic with Acute Exacerbation (295.14), Schizophrenia, Disorganized, in Remission (295.15), Schizophrenia, Disorganized, Unspecified (295.10), Schizophrenia, Paranoid, Subchronic (295.31), Schizophrenia, Paranoid, Chronic (295.32), Schizophrenia, Paranoid, Subchronic with Acute Exacerbation (295.33), Schizophrenia, Paranoid, Chronic with Acute Exacerbation (295.34), Schizophrenia, Paranoid, in Remission (295.35), Schizophrenia, Paranoid, Unspecified (295.30), Schizophrenia, Undifferentiated, Subchronic (295.91), Schizophrenia, Undifferentiated, chronic (295.92), Schizophrenia, Undifferentiated, Subchronic with Acute Exacerbation (295.93), Schizophrenia, Undifferentiated, Chronic with Acute Exacerbation (295.94), Schizophrenia, Undifferentiated, in Remission (295.95), Schizophrenia, Undifferentiated, Unspecified (295.90), Schizophrenia, Residual, Subchronic (295.61), Schizophrenia, Residual, Chronic (295.62), Schizophrenia, Residual, Subchronic with Acute Exacerbation (295.63), Schizophrenia, Residual, Chronic with Acute Exacerbation (295.94), Schizophrenia, Residual, in Remission (295.65), Schizophrenia, Residual, Unspecified (295.60), Delusional (Paranoid) Disorder (297.10), Brief Reactive Psychosis (298.80), Schizophreniform Disorder (295.40), Schizoaffective Disorder (295.70), Induced Psychotic Disorder (297.30), Psychotic Disorder NOS (Atypical Psychosis) (298.90), Bipolar Disorder, Mixed, Severe, without Psychotic Features (296.63), Bipolar Disorder, Manic, Severe, without Psychotic Features (296.43), Bipolar Disorder, Depressed, Severe, without Psychotic Features (296.53), Major Depression, Single Episode, Severe, without Psychotic Features (296.23), Major Depression, Recurrent, Severe, without Psychotic Features (296.33), Bipolar Disorder, Mixed, with Psychotic Features (296.64), Bipolar Disorder, Manic, with Psychotic Features (296.44), Bipolar Disorder, Depressed, with Psychotic Features (296.54), Bipolar Disorder NOS (296.70), Major Depression, Single Episode, with Psychotic Features (296.24), and Major Depression, Recurrent with Psychotic Features (296.34).

Preferably, an effective amount of anhydrous Form I 2-methyl-4-(4-methyl-1-piperazinyl)-10H-thieno-[2,3-b][1,5]benzodiazepine, or an acid addition salt thereof, is used for the treatment of Tourette's Disorder; Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis); Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, with Psychotic Features; Hebephrenic Schizophrenia; Post-Schizophrenic Depression; Delusional Disorder; and Other Persistent Delusional Disorders.

More preferredly, anhydrous Form I 2-methyl-4-(4-methyl-1-piperazinyl)-10H-thieno-[2,3-b][1,5]benzodiazepine is used to treat the following pathologic psychological conditions including Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; Induced Psychotic Disorder; Psychotic Disorder NOS (Atypical Psychosis);Bipolar Disorder, Mixed, with Psychotic Features; Bipolar Disorder, Manic, with Psychotic Features; Bipolar Disorder, Depressed, with Psychotic Features; Bipolar Disorder NOS; Major Depression, Single Episode, with Psychotic Features; Hebephrenic Schizophrenia; Post-Schizophrenic Depression; Delusional Disorder; and Other Persistent Delusional Disorders.

Examples of conditions which are most preferredly treated using anhydrous Form I 2-methyl-4-(4-methyl-1-piperazinyl)-10H-thieno-[2,3-b][1,5]benzodiazepine include Schizophrenia, Catatonic, Subchronic; Schizophrenia, Catatonic, Chronic; Schizophrenia, Catatonic, Subchronic with Acute Exacerbation; Schizophrenia, Catatonic, Chronic with Acute Exacerbation; Schizophrenia, Catatonic, in Remission; Schizophrenia, Catatonic, Unspecified; Schizophrenia, Disorganized, Subchronic; Schizophrenia, Disorganized, Chronic; Schizophrenia, Disorganized, Subchronic with Acute Exacerbation; Schizophrenia, Disorganized, Chronic with Acute Exacerbation; Schizophrenia, Disorganized, in Remission; Schizophrenia, Disorganized, Unspecified; Schizophrenia, Paranoid, Subchronic; Schizophrenia, Paranoid, Chronic; Schizophrenia, Paranoid, Subchronic with Acute Exacerbation; Schizophrenia, Paranoid, Chronic with Acute Exacerbation; Schizophrenia, Paranoid, in Remission; Schizophrenia, Paranoid, Unspecified; Schizophrenia, Undifferentiated, Subchronic; Schizophrenia, Undifferentiated, Chronic; Schizophrenia, Undifferentiated, Subchronic with Acute Exacerbation; Schizophrenia, Undifferentiated, Chronic with Acute Exacerbation; Schizophrenia, Undifferentiated, in Remission; Schizophrenia, Undifferentiated, Unspecified; Schizophrenia, Residual, Subchronic; Schizophrenia, Residual, Chronic; Schizophrenia, Residual, Subchronic with Acute Exacerbation; Schizophrenia, Residual, Chronic with Acute Exacerbation; Schizophrenia, Residual, in Remission; Schizophrenia, Residual, Unspecified; Delusional (Paranoid) Disorder; Brief Reactive Psychosis; Schizophreniform Disorder; Schizoaffective Disorder; and Hebephrenic Schizophrenia.

Examples of anxiety disorders which may more preferredly be treated using an effective amount of anhydrous Form I 2-methyl-4-(4-methyl-1-piperazinyl)-10H-thieno[2,3-b][1,5]benzodiazepine, or an acid addition salt thereof, include Psychoactive Substance Anxiety Disorder; Organic Anxiety Disorder; Obsessive Compulsive Disorder; Post-traumatic Stress Disorder; Generalized Anxiety Disorder; and Anxiety Disorder NOS.

Examples of the anxiety disorders which are most preferredly treated using anhydrous Form I 2-methyl-4-(4-methyl-1-piperazinyl)-10H-thieno-[2,3-b][1,5] benzodiazepine include Organic Anxiety Disorder; Obsessive Compulsive Disorder; Post-traumatic Stress Disorder; Generalized Anxiety Disorder; and Anxiety Disorder NOS.

As used herein the term "Functional Bowel Disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "Functional Bowel Disorder" includes but is not limited to irritable bowel syndrome, hypermotility, ichlasia, hypertonic lower esophogeal sphincter, tachygastria, constipation, hypermotility associated with irritable bowel syndrome.

Functional Bowel Disorders are characterized by abnormal bowel function without detectable structural abnormalities. Abnormal bowel function includes diarrhea, constipation, mucorrhea, and pain or discomfort over the course of the sigmoid colon. Such disorders are influenced by psychological factors and stressful life situations.

The Functional Bowel Disorder, Irritable Bowel Syndrome (IBS), is one of the most commonly encountered gastrointestinal disorders. Between 20% and 50% of patients referred to gastrointestinal clinics suffer from IBS. Symptoms of IBS occur in approximately 14% of otherwise apparently healthy people. IBS is a complex condition, in part because it is not a disease but a syndrome composed of a number of conditions with similar manifestations.

The compound anhydrous Form I 2-methyl-4-(4-methyl-1-piperazinyl)-10H-thieno-[2,3-b][1,5]benzodiazepine has antimuscarinic activity, 5-HT$_{2B}$ receptor activity, and is denoted for use in the treatment of certain gastrointestinal conditions. Thus, the compound is suggested for the treatment of Functional Bowel Disorders including, but not limited to, irritable bowel syndrome, gastric hypermotility, and related conditions.

When anhydrous Form I 2-methyl-4-(4-methyl-1-piperazinyl)-10H-thieno[2,3-b][1,5]benzodiazepine is used for the treatment of gastrointestinal disorders, it is more preferably used for the treatment of irritable bowel syndrome or gastric hypermotility disorder. When treating gastrointestinal disorders using anhydrous Form I 2-methyl-4-(4-methyl-1-piperazinyl)-10H-thieno-[2,3-b][1,5] benzodiazepine, it is most preferably used for the treatment of irritable bowel syndrome.

Further, the solvates of this invention are particularly useful for preparing substantially pure anhydrous Form I olanzapine. Applicants have discovered that anhydrous Form I olanzapine can be prepared by crystallizing a solvate of this invention in an appropriate crystallization solvent. Such solvents are preferredly one or more selected from the group consisting of aromatic solvents, $C_1$–$C_3$ alkyl acetates, and $C_1$–$C_3$ alkyl esters and ethers. Most preferred crystallization solvents are ethyl acetate, tetrahydrofuran, and toluene.

The anhydrous Form I 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from 0.25 to 30 mg, preferably from 1 to 20 mg, per day may be used. A once a day dosage is normally sufficient, although divided doses may be administered. For treatment of central nervous system disorders, a dose range of from 1 to 30 mg, preferably 2.5 to 20 mg per day is suitable. Radiolabelled anhydrous Form I 2-methyl-4-(4-methyl-1-piperazinyl)-10H-thieno-[2,3-b][1,5] benzodiazepine, can be detected in the saliva and thus the compound can potentially be monitored in patients to assess compliance.

The anhydrous Form I 2-methyl-4-(4-methyl-1-piperazinyl)-10H-thieno-[2,3-b][1,5]benzodiazepine compound will normally be administered orally or by injection and, for this purpose, it is usually employed in the form of a pharmaceutical composition.

Accordingly, pharmaceutical compositions comprising anhydrous Form I 2-methyl-4-(4-methyl-1-piperazinyl)-10H-thieno[2,3-b][1,5]benzodiazepine, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient.

Depending on the method of administration, the compositions for the treatment of central nervous system conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 30 mg, more usually 1 to 30 mg, of the active ingredient. When a sustained release formulation is desired, the unit dosage form may contain from 0.25 to 200 mg of the active ingredient. A preferred formulation of the invention is a capsule or tablet comprising 0.25 to 30 mg or 1 to 30 mg of active ingredient together with a pharmaceutically acceptable carrier therefor. A further preferred formulation is an injection which in unit dosage form comprises 0.25 to 30 mg or 1 to 30 mg of active ingredient together with a pharmaceutically acceptable diluent therefor.

The formation of solvates is known to be an individualistic effect. The ability of a given compound to form a solvate is not predictable, to aApplicant's knowledge. Further, the beneficial utility of such solvates is particularly surprising. The present invention provides three crystalline solvates of 2-methyl-4-(4-methyl-1-piperazinyl)-10H-thieno[2,3-b][1,5]benzodiazepine which have been verified using x-ray crystal techniques. The solvates of this invention may be prepared by suspending 2-methyl-4-(4-methyl-1-piperazinyl)-10H-thieno[2,3-b][1,5]benzodiazepine in warm solvent or solvent mixture. Most preferably the solvent temperature is from about 0° C. to 100° C., although other reaction temperatures can be effective with alteration of the reaction conditions using known techniques. A preferred temperature is from about 25° C. to about 50° C. The mixture is most desirably stirred for about 30 minutes or more. The reaction time will vary with the temperature of the reaction, pressure, and with the completion of reaction desired.

The present invention provides a new method for preparing a lower alcohol solvate of olanzapine. The process provides greater yields of the desired product, eliminates tedious separation steps, and provides a product that is easy to handle for production purposes. Formerly, technical grade olanzapine was precipitated by the addition of an excess of water to the reaction mixture. Surprisingly, Applicants have discovered that precipitation of technical grade olanzapine by the addition of a $C_1$–$C_3$ alcohol results in a significantly purer product requiring only one recrystallization. The most preferred alcohols are methanol and ethanol. A particularly preferred alcohol is methanol. The improved features include fewer recrystallizations, the elemination of a hot toluene recrystallization, improved throughput, and enhanced environmental safety.

The solvate may be isolated by cooling the mixture to ambient temperature or through the use of an antisolvent. However, the most preferred isolation method is the lower alcohol process described supra. The solvates are typically dried or azeotroped under ambient conditions; however, other common drying methods can be utilized if they are carefully controlled.

Most preferably, a solvate of this invention is azeotroped and recrystallized in one or more solvents selected from the group consisting of acetone, ethyl acetate, 2-propanol, tetrahydrofuran, toluene, and heptane. A particularly preferred solvent is one containing ethyl acetate.

Surprisingly, the presently claimed process provides a pharmaceutically elegant Form I product having pharmaceutically acceptable color, potency $\geq 97\%$, total related substances $<0.5\%$ and an isolated yield of $>73\%$.

The starting materials for the present invention can be prepared by a variety of procedures well known to those of ordinary skill in the art. The material to be employed as starting materials in the process of this invention can be prepared by the general procedure taught by Chakrabarti in U.S. Pat. No. 5,229,382, ('382) herein incorporated by reference in its entirety.

The olanzapine crude product provided by the methods of the '382 patent typically exhibit a color which is undesired for commercial pharmaceutical use. Carbon treatment of the olanzapine crude product prepared using the '382 methods typically does not remove all of the undesired color. Therefore, greater purity was desired.

As used herein mixing steps may be accomplished using common agitation methods such as stirring, shaking, and the like. As used herein the phrase "producing crystalline product from the mixture" shall refer to crystallization from the stated mixture of compound and solvent. Further, the artisan recognizes that crystallization processes may include seeding, chilling, scratching the glass of the reaction vessel, and other such common techniques.

The concentration of reactants is not critical for the invention. The art worker can alter the concentration of the reactants to achieve the desired rate of reaction and product yield.

The length of time for carrying out the processes described will vary. As is always the case in chemistry, the rate of the reaction depends on a variety of factors, such as the temperature and the exact compound which is to be prepared. The course of the reaction may be followed using methods familiar to the skilled artisan.

Compound characterization methods include, for example, x-ray powder pattern analysis, thermogravimetric analysis (TGA), differential scanning calorimetery (DSC), titrametric analysis for water, and $H^1$-NMR analysis for solvent content.

The following examples are provided for purposes of illustration and are not to be construed as limiting the scope of the claimed invention. As used in the following examples, the term "technical grade 2-methyl-4-(4-methyl-1-piperazinyl)-10H-thieno[2,3-b][1,5]benzodiazepine" shall refer to 2-methyl-4-(4-methyl-1-piperazinyl)-10H-thieno[2, 3-b][1,5]benzodiazepine dried solvate product which requires the final purification step. The term "crude" 2-methyl-4-(4-methyl-1-piperazinyl)-10H-thieno[2,3-b][1, 5]benzodiazepine shall refer to 2-methyl-4-(4-methyl-1-piperazinyl)-10H-thieno[2,3-b][1,5]benzodiazepine which has not been purified by a solvation step.

EXAMPLE 1

Form I from methanolate

A 1.7 g sample of methanol solvate and a 50 mg sample of Form I olanzapine were placed in a mortar and pulverized to a fine powder. The resulting mixture was placed in a vacuum drying oven and dried at 30° C. at 100–300 mm for 18 hours. The temperature of the drying oven was increased to 50° C. and the sample was dried at 50° C. at 100–300 mm for 24 hours. The dried product was identified as Form I 2-methyl-4-(4-methyl-1-piperazinyl )-10H-thieno[2,3-b][1, 5]benzodiazepine using x-ray powder analysis.

EXAMPLE 2

Methanol solvate

A 1.3 mL sample of crude 2-methyl-4-(4-methyl-1-piperazinyl)-10H-thieno[2,3-b][1,5]benzodiazepine in ethyl acetate and methanol (8:2, wt:wt) was placed in a glass vial. The vial and contents were placed inside a larger vial containing silicone oil. The outer vial was sealed and the contents were allowed to stand undisturbed at ambient temperature for about 10 days. The inner vial was retrieved and sealed. The inner vial contents were characterized using X-ray powder diffraction and determined to be the methanol solvate of 2-methyl-4-(4-methyl-1-piperazinyl)-10H-thieno[2,3-b][1,5]benzodiazepine.

EXAMPLE 3

Methanol solvate

A 20 g sample of crude 2-methyl-4-(4-methyl-1-piperazinyl)-10H-thieno[2,3-b][1,5]benzodiazepine was contacted with a 1:1 (vol) mixture of methanol and water. The mixture was heated to 78° C. and maintained at about 78° C. for about 30 minutes. The resulting mixture was allowed to cool to 30° C. The resulting product was isolated by vacuum filtration and dried for about 30 minutes. The sample was studied using x-ray powder analysis and identified as the methanol solvate of 2-methyl-4-(4-methyl-1-piperazinyl)-10H-thieno[2,3-b][1,5]benzodiazepine The thermogravimetric mass loss was 10.1%. Differential Scanning Calorimetry produced an endotherm at 129.7°, 133.3°, and 195.8° C.

EXAMPLE 4

Ethanol solvate

A 2.0 g sample of crude 2-methyl-4-(4-methyl-1-piperazinyl)-10H-thieno[2,3-b][1,5]benzodiazepine was suspended in absolute ethanol. The stirred suspension was heated to 60° C. and maintained at about 60° C. for about 30 minutes. The mixture was allowed to cool to about 25° C. The solid product was isolated by vacuum filtration. The wet cake was allowed to dry at about 25° C. The product was identified as the ethanol solvate of 2-methyl-4-(4-methyl-1-piperazinyl)-10H-thieno[2,3-b][1,5]benzodiazepine using x-ray powder analysis. The thermogravimetric mass loss was 12.7%. Differential Scanning Calorimetry produced an endotherm at 114.8° C. and 196.6° C. Yield: 1.3 g

EXAMPLE 5

Ethanol Solvate

A 2.0 g sample of crude 2-methyl-4-(4-methyl-1-piperazinyl)-10H-thieno[2,3-b][1,5]benzodiazepine was suspended in a (95:5 wt:wt) mixture of ethanol and water. The mixture was stirred and heated to about 60° C. and maintained at about 60° C. for about 30 minutes. The mixture was allowed to cool to about 25° C. The solid product was isolated using vacuum filtration. The wet cake was dried at ambient conditions. The product was identified as the ethanol solvate of 2-methyl-4-(4-methyl-1-piperazinyl)-10H-thieno[2,3-b][1,5]benzodiazepine using x-ray powder analysis. Yield: 1.3 g. Differential Scanning Calorimetry produced an endotherm at 114.8° and 196.6° C.

EXAMPLE 6

1-propanol solvate

A 2.0 g sample of crude 2-methyl-4-(4-methyl-1-piperazinyl)-10H-thieno[2,3-b][1,5]benzodiazepine was suspended in about 30 g of 1-propanol. The mixture was stirred at about 70° C. and maintained at about 70° C. for about 30 minutes. The resulting mixture was cooled to about 25° C. The solid product was isolated using vacuum filtration. The wet cake was dried under ambient conditions. Yield: 1.3 g. X-ray powder analysis demonstrated that the product was propanol solvate of 2-methyl-4-(4-methyl-1-piperazinyl)-10H-thieno[2,3-b][1,5]benzodiazepine. Differential Scanning Calorimetry produced endotherms at 84.4° to 96.9°, 129.1° to 147.4°, and 195.8° C.

EXAMPLE 7

Technical Grade olanzapine

A 20 g sample of crude 2-methyl-4-(4-methyl-1-piperazinyl)-10H-thieno[2,3-b][1,5]benzodiazepine was contacted with a 1:1 (vol) mixture of methanol and water. The mixture was heated to 78° C. and maintained at about 78° C. for about 30 minutes. The resulting mixture was allowed to cool to 30° C. The resulting product was isolated by vacuum filtration and dried for about 30 minutes. The sample was studied using x-ray powder analysis and identified as the methanol solvate of 2-methyl-4-(4-methyl-1-piperazinyl)-10H-thieno[2,3-b][1,5]benzodiazepine The thermogravimetric mass loss was 10.1%. Differential Scanning Calorimetry produced an endotherm at 129.7°, 133.3°, and 195.8° C.

The methanol solvate prepared as described supra. was dried in a vacuum oven at about 50° C. under about 100–300 mm vacuum for a period of about 27 hours. The resulting material was identified as technical grade 2-methyl-4-(4-methyl-1-piperazinyl)-10H-thieno[2,3-b][1,5]benzodiazepine

EXAMPLE 8

Technical Grade olanzapine

A 2.0 g sample of crude 2-methyl-4-(4-methyl-1-piperazinyl)-10H-thieno[2,3-b][1,5]benzodiazepine was suspended in absolute ethanol. The stirred suspension was heated to 60° C. and maintained at about 60° C. for about 30 minutes. The mixture was allowed to cool to about 25° C. The solid product was isolated by vacuum filtration. The wet cake was allowed to dry at about 25° C. The product was identified as the ethanol solvate of 2-methyl-4-(4-methyl-1-piperazinyl)-10H-thieno[2,3-b][1,5]benzodiazepine using x-ray powder analysis. The thermogravimetric mass loss was 12.7%. Differential Scanning Calorimetry produced an endotherm at 114.8° C. and 196.6° C. Yield: 1.3 g The ethanol solvate prepared as described supra. was dried in a vacuum oven at about 50° C. under about 100–300 mm vacuum for a period of about 27 hours. The resulting material was identified as technical grade 2-methyl-4-(4-methyl-1-piperazinyl)-10H-thieno[2,3-b][1,5]benzodiazepine.

EXAMPLE 9

Technical Grade olanzapine

A 2.0 g sample of crude 2-methyl-4-(4-methyl-1-piperazinyl)-10H-thieno[2,3-b][1,5]benzodiazepine was suspended in about 30 g of 1-propanol. The mixture was stirred at about 70° C. and maintained at about 70° C. for about 30 minutes. The resulting mixture was cooled to about 25° C. The solid product was isolated using vacuum filtration. The wet cake was dried under ambient conditions. Yield: 1.3 g. X-ray powder analysis demonstrated that the product was propanol solvate of 2-methyl-4-(4-methyl-1-piperazinyl)-10H-thieno[2,3-b][1,5]benzodiazepine Differential Scanning Calorimetry produced endotherms at 84.4° to 96.9°, 129.1° to 147.4°, and 195.8° C.

The 1-propanol solvate prepared as described supra. was dried in a vacuum oven at about 50° C. under about 100–300 mm vacuum for a period of about 27 hours. The resulting material was identified as technical grade 2-methyl-4-(4-methyl-1-piperazinyl)-10H-thieno[2,3-b][1,5]benzodiazepine

EXAMPLE 10

Technical olanzapine

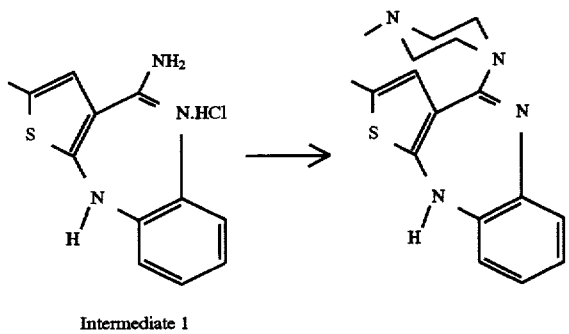

Intermediate 1

In a suitable three neck flask the following was added:
Dimethylsulfoxide (analytical): 6 volumes
Intermediate: 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical olanzapine.

| Yield % | Potency % |
|---|---|
| 76.7 | 98.1 |
| 81.0 | 101.1 |

EXAMPLE 11

Form 1

Intermediate 1 (supra) is suspended in DMSO (3.2 vol.) and toluene (4.5 vol.). A portion (≈0.65 vol.) of the solvent is removed by distillation at 120°–125° C. The mixture is cooled to 110° C., N-methylpiperazine (NMP, 4.2 equiv.) is added and the mixture heated back to reflux (120°–125° C.). Another portion (≅1 vol.) of the solvent is removed by distillation to dry the reaction mixture. A vigorous reflux is desired to drive the reaction to completion (about 7 hrs.) by removing ammonia from the reaction. The product is isolated by the slow addition of water (12.75 vol.) to the cooled (10° C.) reaction solution. The product is collected by filtration and washed with chilled water (2 vol.). The crude olanzapine is dried in vacuo at 60° C. The product is recrystallized from hot toluene (5 vol.) to give a technical grade olanzapine. After drying in vacuo at 50° C., the technical grade olanzapine is recrystallized again from ethyl acetate (10 vol.)/toluene (0.62 vol.)/methanol (3.1 vol.)to give olanzapine as a methanol solvate. The methanol solvate of olanzapine is dissolved at reflux in the ethyl acetate/toluene mixture, filtered hot, and then cooled to 60° C. before methanol is added. The slurry is cooled to 0°–5° C. over 2.5 hrs. The product is collected by filtration and is washed with ethyl acetate. The methanol solvate upon drying at >50° C. is converted to an anhydrous technical grade olanzapine. The anhydrous form is recrystallized from ethyl acetate to provide the desired anhydrous Form I olanzapine.

EXAMPLE 12

Form I using acetone solvent

A 3.0 g sample of technical grade 2-methyl-4-(4-methyl-1-piperazinyl)-10H-thieno[2,3-b][1,5]benzodiazepine was suspended in acetone (30 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 0.8 g.

EXAMPLE 13

Form I using tetrahydrofuran

An 8.0 g sample of technical grade 2-methyl-4-(4-methyl-1-piperazinyl)-10H-thieno[2,3-b][1,5]benzodiazepine was suspended in tetrahydrofuran (25 g). The mixture was stirred and heated to about 60° C. The mixture was maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 1.3 g.

EXAMPLE 14

Form I using ethyl acetate

A 270 g sample of technical grade 2-methyl-4-(4-methyl-1-piperazinyl)-10H-thieno[2,3-b][1,5]benzodiazepine was suspended in ethyl acetate (2.7L). The mixture was heated to about 76° C. and maintained at about 76° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5]benzodiazepine using x-ray powder analysis. Yield: 197 g.

EXAMPLE 15

Form I from t-butanol

A 1.0 g sample of technical grade 2-methyl-4-(4-methyl-1-piperazinyl)-10H-thieno[2,3-b][1,5]benzodiazepine was suspended in tert-butanol (30 g). The stirred mixture was heated to about 60° C. and maintained at about 60° C. for about 30 minutes. The mixture was allowed to cool to about 25° C. The resulting product was isolated using vacuum filtration. The product was identified as Form I 2-methyl-4-(4-methyl-1-piperazinyl)-10H-thieno[2,3-b][1,5] benzodiazepine using x-ray powder analysis. Yield: 0.3 g.

We claim:

1. A process for preparing substantially pure Form I olanzapine comprising drying a $C_1$–$C_3$ alcohol solvate of olanzapine, and then crystallizing the dried solvate with one or more solvents selected from ethyl acetate, acetone, 2-propanol, t-butanol, tetrahydrofuran and toluene.

2. A process of claim 1 wherein the solvate is contacted with the solvent at a temperature from about 25° C. to 80° C.

3. A process of claim 2 wherein the solvent is ethyl acetate.

4. A process of claim 3 wherein the solvate is a mono (methanol) solvate.

5. A process of claim 3 wherein the solvate is a mono (ethanol) solvate or a mono(2-propanol) solvate.

6. A process of claim 2 wherein the solvent is tetrahydrofuran.

7. A process of claim 6 wherein the solvent is mono (methanol) solvate.

8. A process of claim 6 wherein the solvate is a mono (ethanol) solvate or a mono(2-propanol) solvate.

* * * * *